United States Patent [19]

Larkin et al.

[11] Patent Number: 4,606,734

[45] Date of Patent: Aug. 19, 1986

[54] CONTAINER MIXING SYSTEM WITH EXTERNALLY MOUNTED DRUG CONTAINER

[75] Inventors: Mark E. Larkin, Lindenhurst; Ralph M. Quin, Ingleside, both of Ill.

[73] Assignee: Abbott Laboratories, North Chicago, Ill.

[21] Appl. No.: 582,249

[22] Filed: Feb. 22, 1984

[51] Int. Cl.[4] .......................... A61J 1/00; A61M 5/00

[52] U.S. Cl. .......................................... 604/84; 604/86; 604/88; 604/414; 206/222; 222/82

[58] Field of Search ........................ 604/83, 84, 85, 86, 604/87, 88, 89, 92, 411, 414, 416; 222/82, 83, 83.5; 206/222

[56] References Cited

U.S. PATENT DOCUMENTS

| | | | |
|---|---|---|---|
| 2,176,923 | 10/1939 | Nitardy | 604/416 |
| 2,590,900 | 4/1952 | Sommerstein | 604/415 |
| 2,721,552 | 10/1955 | Nosik | 604/416 |
| 2,778,360 | 1/1957 | Miskel | 604/87 |
| 3,290,017 | 12/1966 | Davies et al. | 206/220 |
| 3,306,563 | 2/1967 | Soto | 604/413 |
| 3,532,254 | 10/1970 | Burke | 222/94 |
| 3,636,950 | 1/1972 | Gomez et al. | 604/88 |
| 3,840,136 | 10/1974 | Lanfranconi et al. | 215/6 |
| 3,875,012 | 4/1975 | Dorn et al. | 604/415 |
| 3,915,212 | 10/1975 | Bujan et al. | 604/415 |
| 3,968,872 | 7/1976 | Cavazza | 604/416 |
| 4,048,999 | 9/1977 | Kobel | 604/90 |
| 4,059,112 | 11/1977 | Tischlinger | 604/413 |
| 4,089,432 | 5/1978 | Crankshaw et al. | 604/415 |
| 4,161,178 | 7/1979 | Genese | 604/413 |
| 4,172,457 | 10/1979 | Choksi et al. | 604/416 |
| 4,187,893 | 2/1980 | Bujan | 604/415 |
| 4,289,648 | 9/1981 | Hoskins et al. | 604/416 |
| 4,294,351 | 10/1981 | Cheetham | 206/222 |
| 4,306,554 | 12/1981 | Schwartz et al. | 604/92 |
| 4,392,850 | 7/1983 | Elias et al. | 604/416 |
| 4,405,317 | 9/1983 | Case | 604/90 |
| 4,412,836 | 11/1983 | Brignola | 604/87 |
| 4,417,890 | 11/1983 | Dennehey et al. | 604/256 |
| 4,467,588 | 8/1984 | Carveth | 604/87 |
| 4,515,586 | 5/1985 | Mendenhall et al. | 604/416 |

*Primary Examiner*—Andrew H. Metz
*Assistant Examiner*—O. Chaudhuri
*Attorney, Agent, or Firm*—Robert W. Stevenson; Martin L. Katz

[57] ABSTRACT

A container mixing system wherein a medicament is placed in a container mounted externally of a container with a diluent. Mixing of the medicament in one container with the diluent in the other is accomplished by attaching an additive assembly with a piercing element to an additive port of the diluent container to pierce a diaphragm in the additive port and a diaphragm or stopper in the additive container. In one embodiment, the additive assembly includes a bellows portion which will permit movement of the piercing element through the additive assembly stopper and the port diaphragm while maintaining a sterile medicament in a glass vial.

11 Claims, 5 Drawing Figures

CONTAINER MIXING SYSTEM WITH EXTERNALLY MOUNTED DRUG CONTAINERcBACKGROUND OF THE INVENTION

This invention relates to a container mixing system having manual means to intermix the contents of two containers, one of which is secured outside and in the additive port of the other. More particularly, this invention relates to an additive assembly for a medicament which has a vial container for a medicament wherein the vial is enclosed in a bellows portion and includes a piercing pin which will effect communication between the two containers upon actuation. In this manner the contents of the two containers can be intermixed and the resulting solution administered intravenously to a patient.

Devices providing separate compartments in a container for separately enclosing different components in such a way that they may be later intermixed in a single container are described in U.S. Pat. No. 2,176,923 to Nitardy, U.S. Pat. No. 3,290,017 to Davies, et al. and U.S. Pat. No. 3,532,254 to Burke, et al. These devices are deficient in not being able to maintain an effective seal between the two components to be intermixed. Additionally, in some instances, a barrier between separate chambers does not adequately withstand the rigors of handling and shipping, leading to premature removal. For containers used in health care situations, sterility must be maintained. In U.S. Pat. No. 4,161,178 an additive device employing a pleated collapsible container is disclosed for use in transferring a medicament into a solution container. While many of the prior art devices are simple in configuration the arrangement of parts makes them difficult to sterilize unless the entire device is assembled in a totally sterile environment. Such manufacture is exceedingly expensive.

It is an advantage of the present invention to afford a manually operated container mixing system not subject to the aforementioned disadvantages of the prior art such as those relating to sterility and premature activation. Other advantages are: a manually operable dual container system wherein fluid communication between the containers is effected by means of a slidable piercing spike passing through the stopper of the additive vial and the diaphragm of a flexible container; an activating spike and bellows member for an additive assembly which provides fluid communication with a container additive port; a two container mixing system wherein the container with a medicament can be secured to a flexible container in a sterile manner utilizing standard techniques. Still other advantages of the present invention will become apparent as the description proceeds.

SUMMARY OF THE INVENTION

The foregoing advantages are accomplished and the shortcomings of the prior art are overcome by the present container mixing system wherein two containers initially provide separate sterile compartments for different fluid materials. A first container has wall means to provide a compartment for a first fluid material and a port member with a pierceable diaphragm adopted to be placed in fluid communication with the first container. A second container for a second fluid material is closed by pierceable sealing means with bellows means surrounding it. A guide member extends from the bellows means and is adapted to receive a portion of the first container port. A piercing member has a passage therein and is positioned in the guide member. The bellows means is operatively positioned in conjunction with the second container, the pierceable sealing means and the piercing member to effect movement of the pierceable sealing means with respect to said piercing member. When the guide member is positioned in fluid communication with the container port member and a force is directed on the bellows in the direction of the first container, a piercing of the pierceable sealing means and said port diaphragm is effected with delivery of the second fluid material into the first container for mixing with the first fluid material.

BRIEF DESCRIPTION OF THE DRAWINGS

A better understanding of the two container mixing system of this invention will be had by reference to the drawings wherein.

DESCRIPTION OF THE EMBODIMENTS

Figure 2:
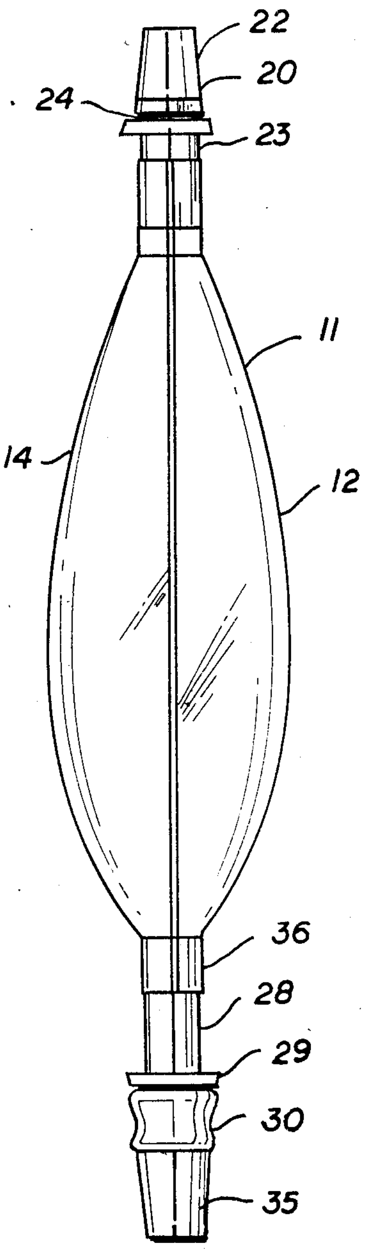
FIG. 2 is a side view in elevation of the container shown in FIG. 1.
Figure 1:
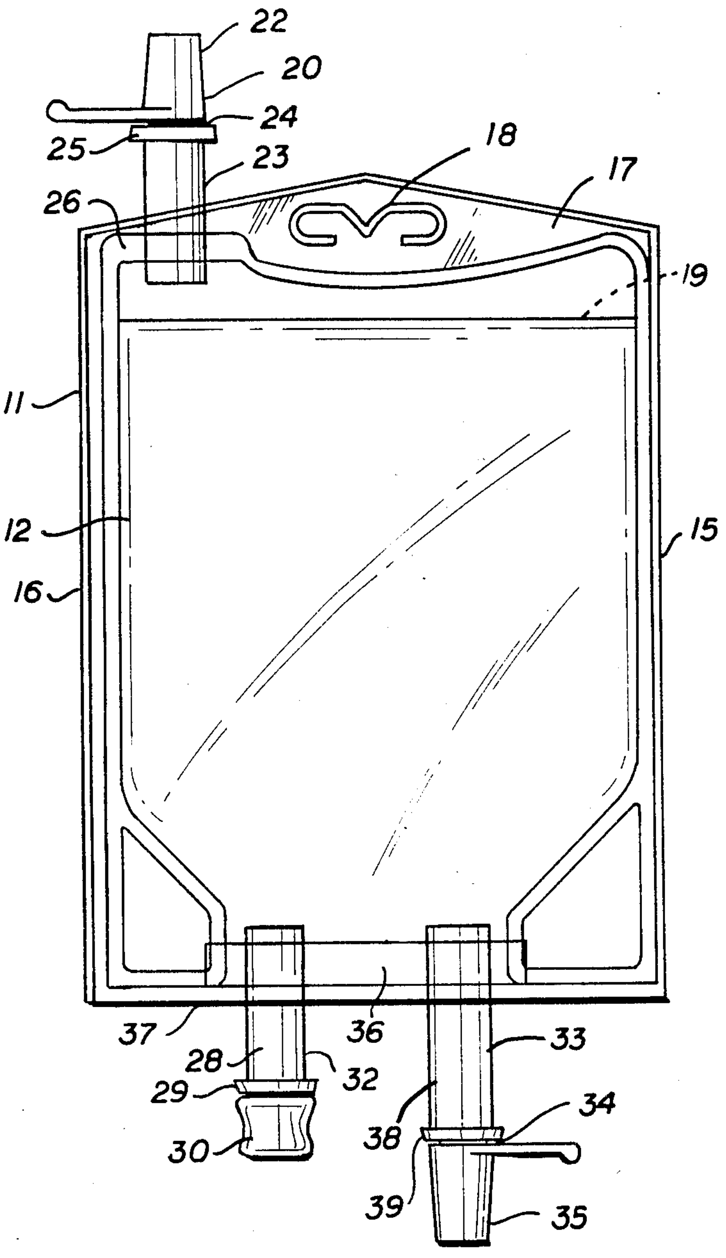
FIG. 1 is a view in front elevation illustrating a flexible container for use in the container mixing system of this invention.
Figure 3:
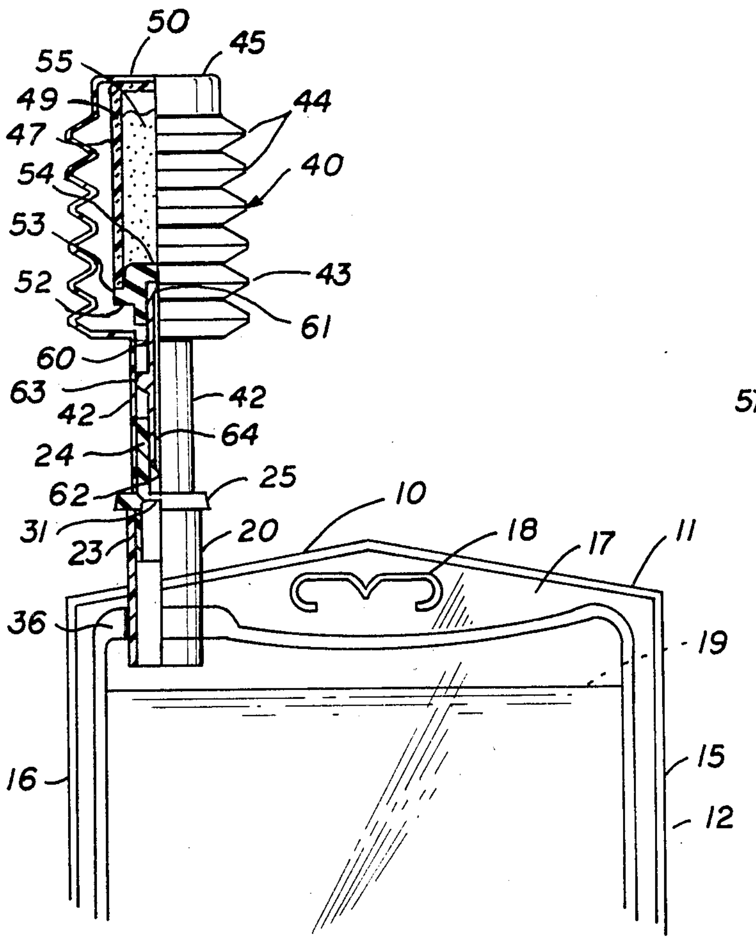
FIG. 3 is a partial view similar to FIG. 1 illustrating the flexible container with the additive assembly attached thereto and with portions broken away depicting the container mixing system prior to activation.

Referring to FIGS. 1–3 of the drawings, the container mixing system generally 10 will include a flexible container 11 having a front wall 12 as well as side walls 15 and 16 forming a typical flexible plastic bag suitable for a sterile I.V. solution 19. Container 11 includes a top wall 17 with a hanger slot 18. An additive port 20 extends through wall 17 and is sealed therein by means of a mandrel seal 26. Port 20 includes the usual outer tubular member 23 to which is sealed an inner tubular member 24 with flange 25. A protective cap 22 is positioned over tubular member 24. In a similar manner, additive port 28 with tubular member 32 extends through end wall 37 and is sealed therein by mandrel seal 36. A reseal plug 30 is positioned over an inner tubular member (not shown) with flange 29. Administration port 33 is similar to port 20 with tubular member 38 extending through seal 36 and including an inner tubular member 34 with flange 39 covered by cap 35.

In FIG. 3, the container mixing system 10 with the additive assembly generally 40 is shown as being placed in conjunction with port 20 of container 10. Additive assembly 40 includes a tubular guide portion 42 extending from bellows member 43 having the usual flexible pleats 44. An end portion 45 is placed in contact with end wall 50 of vial 47 having a side wall 49 for sealing with stopper 52 by means of flange 53. Stopper 52 includes a diaphragm section 54 for piercing by point 61 of piercing member 60. Piercing member 60 has a passage 64 extending between points 61 and 62 and a flange 63 projects from piercing member 60 for seating and slidable engagement in tubular portion 42.

Figure 5:
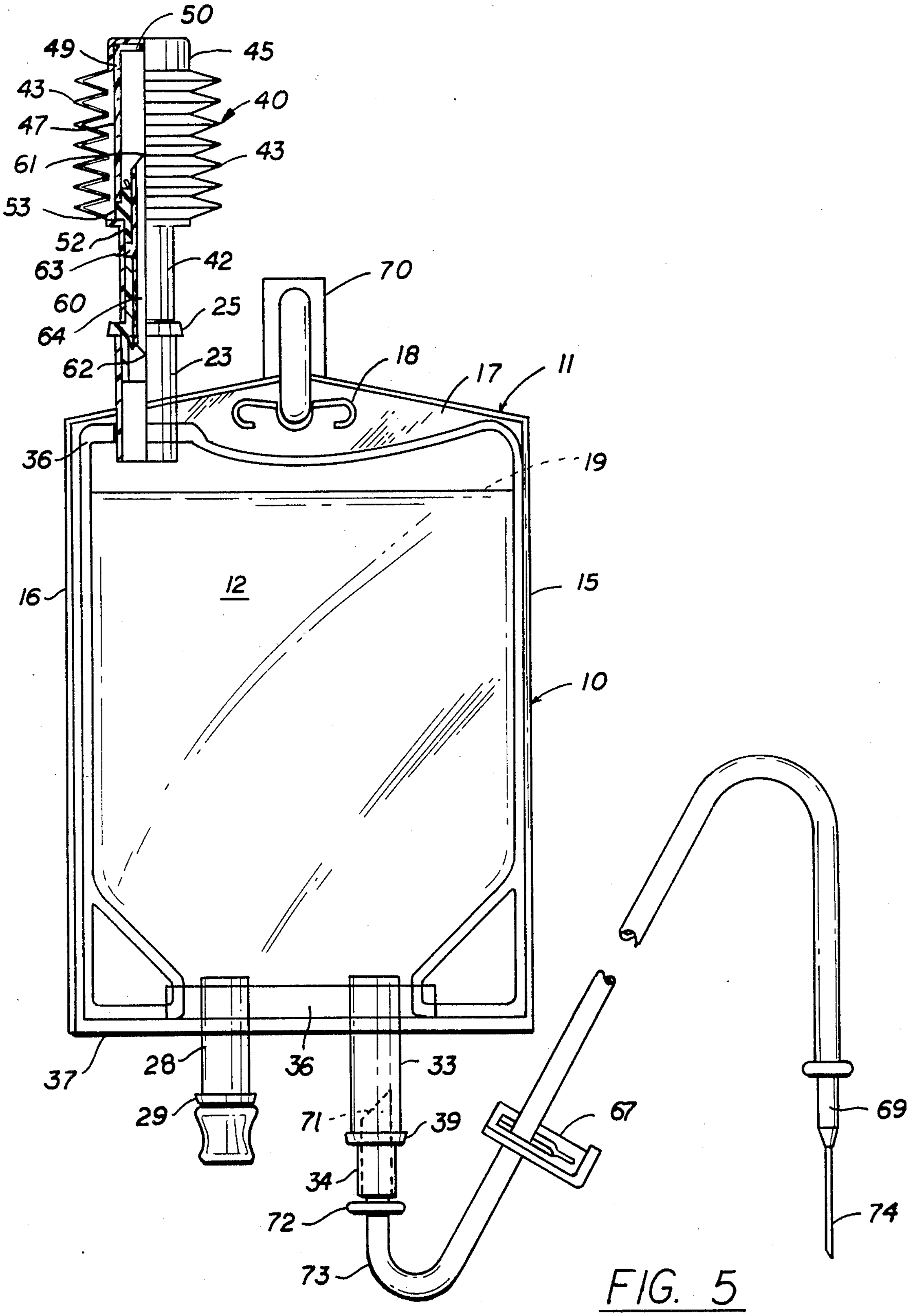
FIG. 5 is a view similar to FIG. 1 illustrating the activation of the container mixing system as well as being interconnected to an I.V. administration set.

Referring to FIG. 5, it will be seen that container 11 with additive assembly 40 in fluid communication therewith is supported by the usual support hook 70 passing through hanger slot 18. Administration port 33 will receive the usual piercing pin spike 71 with flange 72 composing the usual administration set which will include tubing 73, on-off slide clamp 67, as well as hypodermic needle 74 and hub 69.

OPERATION

Figure 4:
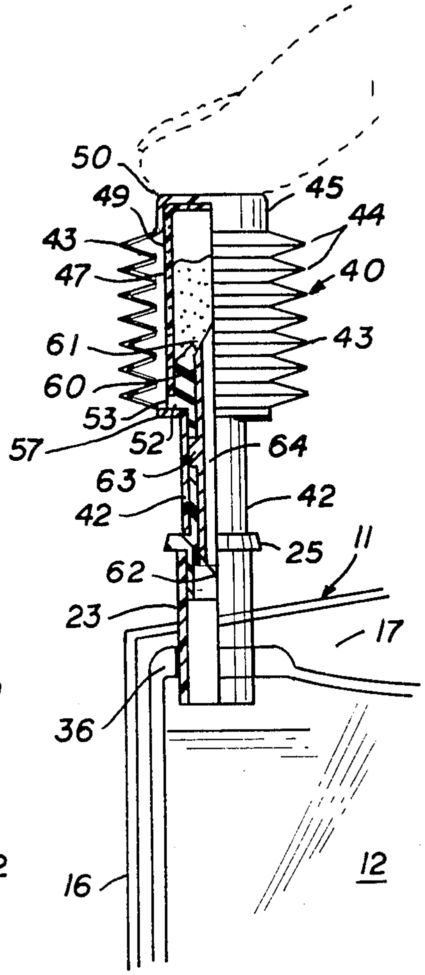
FIG. 4 is a view similar to FIG. 3 showing the container mixing system being activated.

A better understanding of the advantages of container mixing system 10 will be had by a description of its operation. Referring to FIGS. 1 and 2, container 11 will be fabricated in the usual manner from opposing sheets of thermoplastic material which will be sealed such as to form side walls 15 and 16 as well as with top wall 17 and end wall 37 and with mandrel seals 26 and 36 to secure ports 20, 33 and 28. Container 10 will be filled with I.V. liquid through one of the ports 20 or 33 in a customary manner. With reference to FIGS. 3 and 4, additive assembly 40 will have a solid or flowable medicament 55 which can be an antibiotic powder, placed in inner vial member 47 and stopper 52 with flange 53 sealed over the end of side wall 49. Stoppered vial member 47 will be sterilized such as by radiation and placed in bellows member 43 such as by insertion and pinch off. A protective cap similar to cap 22 will be placed over tubular portion 42.

When it is desired to activate container system 10, cap 22 will be removed from port 20 and the cap from tubular portion 42. Tubular portion 42 will be placed over tubular member 24 of port 20. The additive assembly 40 will assume a position as indicated in FIG. 3. To effect a piercing of diaphragm section 54 of stopper 52 as well as diaphragm 31 in port 20 the bellows member will be grasped by a hand in the manner indicated in FIG. 4. The compression of the flexible pleats 44 will cause stopper flange 53 to be seated against shoulder 57 of bellows member 43. Simultaneously, tubular portion 42 will slide over port tubular member 24 until it comes to rest against flange 25 as shown in FIG. 4. Subsequently, stopper 52 will move to contact flange 63 of piercing member 60 and flange 63 will slide in tubular guide 42 and contact tubular member 24. This movement is illustrated in FIG. 4 and will effect the piercing of stopper 52 and port diaphragm 31. Fluid communication between vial 47 and container 10 will be accomplished through passageway 64 of piercing pin 60. Powder 55 will flow into the passageway and liquid 19 can be forced into the vial 47 by squeezing container 11. To effect complete mixing, air from container 11 can also be forced into vial 47 by squeezing container 11 when it is in an upright position such as shown in FIGS. 4 and 5. After thorough mixing, the mixed solution can be administered in the normal manner with the I.V. administration set including piercing pin 71 and hypodermic needle 74 as also shown in FIG. 5.

The present container mixing system 10 has been preferably described for use with a powdered medicament 55 in the vial container 47 and a liquid in container 11. It is obvious that the vial container 47 is usable with any fluid material. For example, a liquid could be placed in the vial container 47 as well as in container 11 with the diluent. Further, while the present container mixing system has been described for use with fluid materials in the health care field, it will be appreciated that the container mixing system can be applied to other fields. For example, it would have application with any fluid materials where it is necessary to maintain two materials in a separate condition until prior to mixing and use, and where one of the materials is sensitive to ambient conditions of the other material. It should be further understood that the term "fluid material" as employed in the specification and claims, is meant to imply any material including a medicament or diluent material which will flow from one compartment to another, whether liquid, solid, or gas.

The preferred material for manufacturing the container 11 is a polyvinylchloride resinous plastic material. However, other resinous plastics such as polypropylene or polyester could be used. The preferred material for composing bellows member 43 and tubular portion 42 is PVC. However, other semirigid plastic materials such as polyethylene, polypropylene could be likewise utilized. Piercing pin 60 is injection molded from a polycarbonate material. If desired, an acetal could be employed. The pierceable stopper 52 is of the standard butyl rubber variety. However, rubber-like plastics such as styrene-butadiene polymers could be substituted.

While bellows member 43 has been illustrated as surrounding vial 47, it will be appreciated that activation of the container mixing system could be effected with the bellows extending over a portion of vial 47.

It will thus be seen that through the present invention there is now provided a manually operated container mixing system which is easily utilized and manufactured. The container system of this invention affords a sterile environment for the fluid materials of various types during storage as well as mixing. Activation of the system is readily accomplished without the use of additional components, and with readily available components.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

What is claimed is:

1. A container mixing system for separately storing a component for subsequent mixing with the fluid contents of a container comprising:

a flexible plastic container having wall means defining a compartment for a first fluid material and a port member with a pierceable diaphragm;

a rigid container for a second fluid material adapted to be placed in fluid communication with said flexible plastic container;

pierceable sealing means closing said rigid container;

flexible enclosure means sealingly enclosing said rigid tubular container;

a guide member extending from said enclosure means adapted to receive a portion of said flexible plastic container port; and a piercing member having a passage therein positioned in said guide member;

said enclosure means operatively positioned in conjunction with said rigid container, said pierceable sealing means and said piercing member to effect movement of said pierceable sealing means with respect to said piercing member;

so that when said guide member is positioned in fluid communication with said flexible plastic container port member and a force is directed on said flexible enclosure means and in the direction of said flexible plastic container, a piercing of said pierceable sealing means of said rigid tubular container and said port diaphragm of said flexible plastic container will be effected along with delivery of said second fluid material from said rigid tubular container into said flexible plastic container for mixing with said first fluid material.

2. The container mixing system as defined in claim 1 wherein said first fluid material is a sterile liquid.

3. The container mixing system as defined in claim 2 wherein said second fluid material is a sterile powder.

4. The container mixing system as defined in claim 1 wherein said piercing member is defined by a piercing pin member having a flange for slidable engagement with said guide member.

5. The container mixing system as defined in claim 1 wherein said enclosure means is joined to said guide member by a shoulder portion and said pierceable sealing means includes a flange for seating engagement with said shoulder portion.

6. The container mixing system as defined in claim 5 wherein said guide member is of a tubular configuration.

7. An additive container assembly for intermixing components in a flexible container for an intravenous fluid having a port member with a pierceable diaphragm comprising:

a rigid container for an additive fluid material;

pierceable sealing means closing said rigid container;

flexible enclosure means sealingly extending over a portion of said rigid container;

a guide member extending from said enclosure means adapted to receive a portion of said port member;

a piercing member having a passage therein positioned in said guide member;

said enclosure means operatively positioned in conjunction with said rigid container, said pierceable sealing means and said piercing member effecting movement of said pierceable sealing means with respect to said piercing member;

so that when said guide member is positioned in fluid communication with the flexible container port member and a force is directed on said flexible enclosure means and in the direction of the flexible container, a piercing of said pierceable sealing means and said port diaphragm and delivery of said fluid material into said flexible container for mixing with said fluid material will be effected.

8. The rigid container assembly as defined in claim 7 wherein said piercing member is defined by a piercing pin having a flange for slidable engagement with said guide member.

9. The rigid container assembly as defined in claim 8 wherein said rigid container is a glass vial and said pierceable sealing means is positioned over an open mount portion thereof.

10. The additive container assembly as defined in claim 9 wherein said enclosure means is joined to said guide member by a shoulder portion and said pierceable sealing means includes a flange for seating engagement with said shoulder portion.

11. The additive container assembly as defined in claim 10 wherein said guide member is of a tubular configuration.

* * * * *